United States Patent [19]

Papenfuhs

[11] 4,252,963

[45] Feb. 24, 1981

[54] PROCESS FOR THE MANUFACTURE OF 2-AMINO-ARYLENO-THIAZOLE COMPOUNDS AND OF DERIVATIVES THEREOF N-SUBSTITUTED IN THE RING

[75] Inventor: Theodor Papenfuhs, Frankfurt am Main, Fed. Rep. of Germany

[73] Assignee: Hoechst Aktiengesellschaft, Fed. Rep. of Germany

[21] Appl. No.: 5,798

[22] Filed: Jan. 23, 1979

[30] Foreign Application Priority Data

Jan. 18, 1978 [DE] Fed. Rep. of Germany ....... 2801991
Aug. 9, 1978 [DE] Fed. Rep. of Germany ....... 2834852
Oct. 18, 1978 [DE] Fed. Rep. of Germany ....... 2845250

[51] Int. Cl.$^3$ ............................................ C07D 272/82
[52] U.S. Cl. .................................... 548/161; 548/164
[58] Field of Search ........................ 260/305; 548/161

[56] References Cited

PUBLICATIONS

Elderfield, Heterocyclic Compounds, vol. 5, Wiley, N.Y., NY, (1957), p. 584.
Finar, Organic Chemistry, vol. 1, Longmans Green, N.Y., (1959), p. 184.

*Primary Examiner*—Donald G. Daus
*Assistant Examiner*—D. B. Springer
*Attorney, Agent, or Firm*—Connolly and Hutz

[57] ABSTRACT

2-Amino-aryleno-thiazoles in which the amino group in 2-position can be substituted by aryl, alkyl and/or cycloalkyl, and 2-imino-aryleno-thiazolines substituted at the ring nitrogen by aryl, alkyl or cycloalkyl are produced by cyclization of arylthioureas carrying corresponding substituents at the respective nitrogen atom, using thionyl chloride as cyclization agent. The advantage of the improved process resides in that the amount of sulfur formed is very low and that the other by-products are easy to separate and can be used further. The thiazoles and thiazolines are obtained in a high yield and purity. They are valuable starting compounds, especially for the manufacture of dyestuffs.

4 Claims, No Drawings

PROCESS FOR THE MANUFACTURE OF 2-AMINO-ARYLENO-THIAZOLE COMPOUNDS AND OF DERIVATIVES THEREOF N-SUBSTITUTED IN THE RING

The present invention is an improvement in a process for the manufacture of intermediates used, for example, as starting substances, especially for the manufacture of azo dyestuffs. More particularly, it relates to an improved process for the manufacture of 2-amino-arylenothiazoles and derivatives thereof N-substituted in the heterocycle, i.e. of 2-imino-aryleno-thiazolines, by cyclization of N-aryl-thio-ureas, N'-substituted N-arylthio-ureas or N-substituted N-aryl-thio-ureas.

2-Amino-aryleno-thiazoles such as 2-aminobenzthiazoles and 2-aminonaphthothiazoles, the 2-N-substituted derivatives thereof and 2-imino-aryleno-thiazolines substituted at the ring nitrogen, are valuable starting components for azo dyestuffs and plant protecting agents. They can be produced by oxidative cyclization of N-aryl-thioureas, N'-substituted N-aryl-thioureas or N-substituted N-aryl-thioureas. As cyclization agents there have been proposed bromine and bromine chloride (BrCl), bromine in chloroform or acetic acid (Journal für praktische Chemie [2] 153, 1 (1939); Org.Synthesis 27, 53 (1947); J.Chem.Soc. 1926, 2951 and 2958; J.Chem.Soc. 1927, 1209); chlorine in ethylene dichloride with bromine as catalyst (German Offenlegungsschrift No. 2,631,163); sulfur chloride ($S_2Cl_2$), sulfuryl chloride ($SO_2Cl_2$) and sulfur dichloride ($SCl_2$); in industry mostly sulfur chloride is used (cf. BIOS 1149, pages 83; J.Chem.Soc.London (C), 1969, page 268; German Offenlegungsschrift No. 1,916,599; Elderfield, Heterocyclic Compounds, volume 5, pages 581 et seq. (1957); French Pat. No. 688,867). In these processes organic solvents are used; however, in industry, the use of such solvents is avoided as long as possible. A mode of cyclization in the absence of solvents has been proposed in German Offenlegungsschrift No. 2,601,700, but it has not gained any industrial importance because of the use of an at least tenfold excess of disulfur chloride. The known processes carried out on an industrial scale with the use of sulfur chloride are especially disadvantageous in that resins are formed, high amounts of sulfur of about 7 mols for each mol of 2-amino-aryleno-thiazole or 2-imino-aryleno-thiazoline are obtained and a time-consuming regeneration of the solvent or steam distillation are required.

It has now been found that 2-amino-arylenothiazoles, derivatives thereof substituted at the nitrogen atom of the heterocyclic ring and 2-amino-arylenothiazoles substituted at the nitrogen atom of the amino group in 2-position can be produced in much simpler manner by cyclization or corresponding aryl-thioureas when the cyclization is carried out with thionyl chloride.

The chemical reaction according to the invention takes places in a manner such that 2 mols of aryl-thiourea react with 4 mols of thionyl chloride and 2 mols of water to give 2 mols of the 2-amino-aryleno-thiazole hydrochloride or N-substituted 2-imino-aryleno-thiazoline hydrochloride or 2-N-substituted 2-amino-thiazole hydrochloride, 3 mols of sulfur dioxide, 1 mol of sulfur and 6 mols of hydrogen chloride. Thus, the amount of sulfur obtained is very small and the other reaction products can be readily separated.

The 2-amino-aryleno-thiazoles unsubstituted at the nitrogen atom of the ring can also be designated in their tautomeric form as 2-imino-aryleno-thiazolines according to the following tautomeric equation:

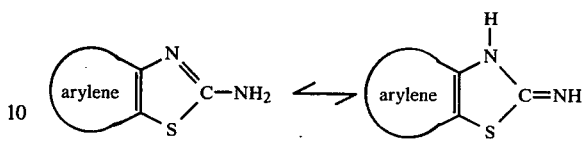

Hence, the present invention provides an improved process for the manufacture of 2-amino-arylenothiazoles, the derivatives thereof N-substituted in the thiazoline ring by alkyl, cycloalkyl or aryl, i.e. the imino-aryleno-thiazolines, and of 2-amino-arylenothiazoles in which the amino group in 2-position is substituted by alkyl, cycloalkyl and/or aryl, by cyclization of N-aryl-thioureas, N-aryl-N-alkyl-, N-aryl-N-cycloalkyl-, N,N-diaryl-thioureas, N-aryl-N'-alkyl-, N-aryl-N'-cycloalkyl-, N-aryl-N',N'-dialkyl-, N-aryl-N'-alkyl-N'-cycloalkyl, N,N'-diaryl-N'-alkyl-, or N,N'-diaryl-thioureas, which comprises carrying out the cyclization by means of thionyl chloride. As starting materials compounds of the following formulae (1A) and (1B)

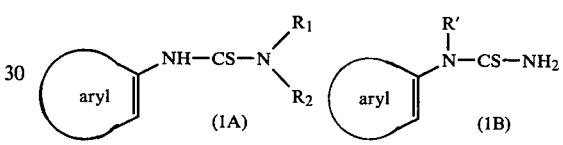

are used, from which the thiazoles and thiazolines of the formulae (2A) and (2B) are produced.

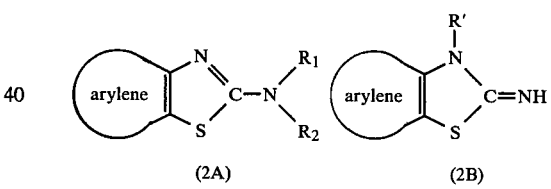

In the above formulae "aryl" denotes a monovalent, carbocyclic or heterocyclic aromatic radical which is unsubstituted or substituted by electro-neutral, electro-positive and/or weakly electro-negative substituents; "arylene" denotes a carboxylic or heterocyclic aromatic radical being bivalent in ortho-position, which is unsubstituted or substituted by electro-neutral, electro-positive and/or weakly electro-negative substituents; $R_1$ and $R_2$, which are identical or different, denote hydrogen, alkyl, cycloalkyl, or aryl; and R' denotes hydrogen, alkyl, cycloalkyl, or aryl.

The process of the invention proceeds according to the following reaction equation (demonstrated for the basic aryl-thioureas):

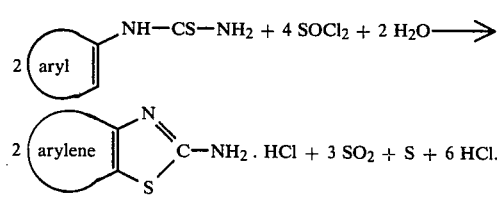

Suitable electro-positive or electro-neutral substituents are, for example lower alkyl groups, such as methyl, ethyl and propyl, the hydroxy group, lower alkoxy groups, such as methoxy, ethoxy, propoxy and butoxy; amino and acylamino groups each optionally substituted by lower aliphatic radicals or aryl radicals, such as phenyl, for example lower alkylamino, di-lower alkyl amino; phenylamino, N-methyl-phenylamino, and acylamino groups of lower aliphatic carboxylic acids or of arylcarboxylic acids such as benzoic acid; lower alkylmercapto and acyloxy groups of lower aliphatic carboxylic acids or arylcarboxylic acids, such as benzoic acid. Weakly electro-negative groups are, for example, halogen atoms, such as fluorine, chlorine or bromine, lower alkanoyl and lower alkoxycarbonyl.

The aryl and arylene radicals in the sense of this invention are preferably phenyl and naphthyl and phenylene and naphthylene radicals. Preferred cycloalkyl radicals are cyclopentyl and cyclohexyl which may be substituted by 1 to 3 methyl radicals. Preferred alkyl radicals are lower alkyl radicals. The term "lower" indicated in the instant specification denotes groups the alkyl or alkylene radicals of which have from 1 to 6 and preferably from 1 to 4 carbon atoms.

The present invention preferably relates to the manufacture of compounds of formulae (2A) and (2B) in which "arylene" denotes phenylene or naphthylene which may be substituted by 1, 2 or 3 electro-neutral, electro-positive and/or weakly electro-negative substituents, preferably by 1, 2 or 3 substituents selected from the group of lower alkyl, hydroxy, lower alkoxy; amino optionally substituted by lower alkyl and/or phenyl; lower alkanoylamino, benzoylamino, lower alkylmercapto, lower alkanoyl, benzoyl, fluorine, chlorine, bromine, lower alkanoyloxy and lower alkoxycarbonyl; $R_1$ and $R_2$ are identical or different and $R_1$ is hydrogen, alkyl having from 1 to 8 carbon atoms unsubstituted or substituted by halogen, for example fluorine, chlorine or bromine, lower alkoxy, such as methoxy or ethoxy, or by phenyl, the phenyl radical possibly containing 1, 2 or 3 electro-neutral, electro-positive and/or weakly electro-negative substituents, or $R_1$ is cycloalkyl; $R_2$ is hydrogen or alkyl having from 1 to 8 carbon atoms unsubstituted or substituted by halogen, such as fluorine, chlorine or bromine, or by lower alkoxy, such as methoxy or ethoxy, or by phenyl, the phenyl optionally may contain 1, 2 or 3 electro-neutral, electro-positive and/or weakly electro-negative substituents, or $R_2$ is cycloalkyl or aryl; and $R'$ denotes hydrogen, aryl, cycloalkyl or alkyl. Preferred starting materials of formulae (1A) and (1B) are compounds in which "aryl" denotes phenyl or naphthyl optionally substituted by 1, 2 or 3 electro-neutral, electro-positive and/or weakly electro-negative substituents, preferably by 1, 2 or 3 substituents selected from the group consisting of lower alkyl, hydroxy, lower alkoxy, amino optionally substituted by lower alkyl and/or phenyl, lower alkanoylamino, benzoylamino, lower alkylmercapto, lower alkanoyl, benzoyl, fluorine, chlorine, bromine, lower alkanoyloxy and lower alkoxycarbonyl; and $R_1$, $R_2$ and $R'$ have the above meanings.

The process of the invention takes a uniform course and high yields of analytically pure 2-amino-arylenothiazoles, 2-N-substituted derivatives thereof and 2-imino-aryleno-thiazoline compounds N-substituted in the thiazoline ring are obtained. It is especially suitable to the manufacture of 2-imino-benzothiazolines N-substituted in the thiazoline ring, of 2-aminobenzothiazoles and 2-aminonaphthothiazoles substituted or unsubstituted at the nitrogen atom in 2-position and the derivatives thereof substituted in the benzene nuclei by electro-neutral, electro-positive and/or weakly electro-negative groups; the N-substituents preferably being lower alkyl radicals. The compounds of these types are produced from corresponding NH- or N- or N'-substituted N-phenyl or N-naphthyl-thioureas which are unsubstituted or substituted in the aromatic nucleus by the aforesaid groups.

It is especially preferred to produce by the process of the invention 2-aminobenzthiazole compounds of formula (2a) or 2-iminobenzthiazoline compounds of formula (2b)

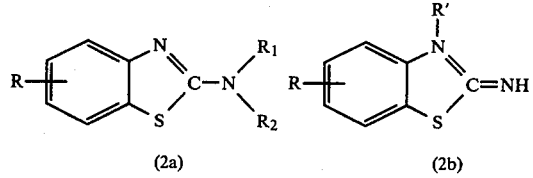

(2a)                    (2b)

in which R denotes hydrogen, fluorine, chlorine or bromine, or lower alkyl, such as methyl or ethyl, or lower alkoxy, such as methoxy or ethoxy, hydroxy, or amino; $R_1$ and $R_2$ are identical or different from each other and $R_1$ denotes hydrogen and $R_2$ denotes hydrogen, lower alkyl, such as methyl, ethyl, propyl, or butyl; or cycloalkyl, such as cyclohexyl; or aryl, preferably phenyl, optionally substituted by 1, 2 or 3 of the aforesaid electro-neutral, electro-positive and/or weakly electro-negative substituents, for example by 1 or 2 substituents selected from the group of methyl, ethyl, methoxy, ethoxy and chlorine, $R_1$ and $R_2$ preferably both being hydrogen; $R'$ denotes hydrogen or alkyl of from 1 to 4 C-atoms, optionally being substituted by phenyl, hydroxy or an amino group of the formula $—NR_3R_4$ in which $R_3$ and $R_4$ can be identical or different from each other and $R_3$ denotes alkyl of from 1 to 4 C-atoms, benzyl or phenyl; and $R_4$ denotes $C_1$–$C_4$ alkyl, or $R'$ denotes cycloalkyl, preferably cyclohexyl, or aryl such as phenyl optionally substituted by the aforesaid electro-neutral, electro-positive and/or weakly electro-negative substituents. Thus, to produce compounds of formula (2), thiourea compounds of the formula (1)

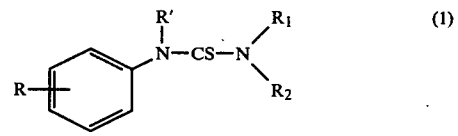

are used as starting compounds in which R, R', $R_1$ and $R_2$ have the aforesaid meaning with the proviso that R' must be hydrogen if $R_1$ or $R_2$ or both are different from hydrogen.

The process according to the invention can be carried out in an organic solvent such as toluene, chlorobenzene or dichlorobenzene. It proved advantageous, however, to operate in the absence of an organic solvent and to use at least two times the molar amount of thionyl chloride, calculated on the arylthiourea used as starting compound. The reaction is preferably carried out in thionyl chloride as solvent or reaction medium, using for each mol of arylthiourea of formula (1) about 2.1 to 5 mols, preferably 2.5 to 3 mols of thionyl chloride.

It is possible, of course, to use a higher excess of thionyl chloride, but this is not very advantageous for economical and ecological reasons.

According to a preferred embodiment of the process of the invention, the starting arylthiourea is added while stirring to the thionyl chloride at a temperature in the range of from 10° to 70° C., preferably 10° to 55° C., and the reaction is carried out for some hours, for example about 3 to 5 hours, at a temperature of from about 40° to 80° C., preferably 50° to 65° C. A melt is obtained which is slowly decomposed either by adding water or by slowly adding the melt to water. In this manner an aqueous solution of the hydrochloride of 2-aminoaryleno-thiazole or 2-imino-aryleno-thiazoline is obtained in which the sulfur formed in the reaction is suspended.

The gases consisting of sulfur dioxide and hydrogen chloride formed in the cyclization according to the invention, and the subsequent hydrolysis are advantageously absorbed first in water and then in aqueous alkali metal hydroxide solution, for example an aqueous sodium hydroxide solution. The aqueous hydrochloric acid and sodium bisulfite solution obtained in this manner can be used in numerous industrial processes. Thus, the waste products can be recycled and do not affect the ecology balance of the improved process of the invention.

After separation from the suspended sulfur by filtration, the aqueous solution of 2-aminoarylenothiazole hydrochloride or 2-iminoarylenothiazoline hydrochloride is clarified by means of a charcoal, whereupon the 2-aminoarylenothiazole or 2-iminoarylenothiazoline is precipitated by the addition of a basic neutralizing agent such as ammonia or a hydroxide, oxide or carbonate of an alkali metal or alkaline earth metal, for example of sodium, potassium, or calcium; aqueous ammonia is preferred. The precipitated thiazole or thiazoline of formula (2) is then isolated by filtration or centrifugation.

The thiazoles and thiazolines of formulae (2) are obtained by the process of the invention in a high purity and yield. As compared to industrially practiced processes, the amount of sulfur formed is reduced to less than one fifth. The process of the invention has the further advantage that it can be carried out in simple apparatus which require little space only, and in the absence of an organic solvent.

The starting compounds of formula (1A) can be prepared, for example, by reacting corresponding aryl-isothiocyanates (mustard oils) with primary and secondary amines according to the equation

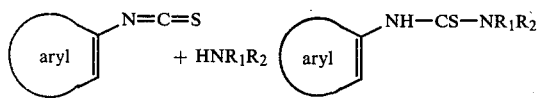

(cf. Houben-Weyl, Methoden der organischen Chemie, Volume IX, pages 889 et seq. (1955)).

The following examples illustrate the invention, the parts and percentages being by weight unless otherwise stated.

EXAMPLE 1

364 Parts of 4-methoxyphenylthiourea are uniformly added, over a period of 2 hours and at a temperature of 50° to 60° C., to 666.4 parts of thionyl chloride and the suspension obtained is stirred for 4 hours at 50° to 60° C. The escaping reaction gases (sulfur dioxide and hydrogen chloride) are transformed into aqueous hydrochloric acid and sodium sulfite solution.

The cyclization melt is then poured, while stirring, into a mixture of 2,700 parts of water and 40 parts of kieselguhr, the mixture is stirred for 30 minutes at 60° C., clarified with 10 parts of charcoal, the latter is filtered off and the solution is added to 350 parts of 25% aqueous ammonia solution. The 6-methoxy-2-aminobenzthiazole precipitates in the form of colorless crystals, which are filtered off, washed with water and dried. 354.6 Parts (96.0% of the theory) of 6-methoxy-2-aminobenzthiazole melting at 162° C. and having a degree of purity of 99.5%, determined by potentiometric titration with perchloric acid, are obtained.

EXAMPLE 2

The reaction is carried out as described in the preceding Example with the exception that instead of 4-methoxyphenylthiourea the equimolar amount of 4-ethoxyphenylthiourea is used. 6-Ethoxy-phenylthiourea melting at 174° C. is obtained in a 95.6% yield and with the same good purity.

EXAMPLE 3

166 Parts of 2-methylphenylthiourea are uniformly added at 20° to 30° C. over a period of 3 hours to 298.7 parts of thionyl chloride. During the course of 2 hours the reaction mixture is heated to 45° to 50° C. and stirring is continued for 3 hours at said temperature. 250 Parts of water are added dropwise to the reaction product over a period of 2 hours, while the temperature is maintained at 50° to 60° C. The escaping reaction gases are absorbed as described in Example 1. The suspension formed is then stirred into a mixture of 1,000 parts of water and 20 parts of kieselguhr, 5 parts of charcoal are added and the whole is stirred for 30 minutes at about 60° C. The mixture is filtered off and the filtrate is adjusted to pH 8.5 by adding dropwise an aqueous about 30% sodium hydroxide solution. The precipitate formed is filtered off with suction at 20° C., washed with water and dried.

155.5 Parts (94.8% of the theory) of 4-methyl-2-amino-benzothiazole melting at 136° C. and having a purity of over 99.5% are obtained.

The 4-methyl-2-aminobenzthiazole can be obtained from the reaction melt in an equally good yield and quality by forcing the melt into 1,250 parts of water containing 20 parts of kieselguhr, the other conditions being the same.

EXAMPLE 4

167 Parts of 4-aminophenylthiourea are introduced over a period of 4 hours while stirring into 394.4 parts of thionyl chloride having a temperature of about 50° C., stirring is continued for 4 hours at about 50° C. and the cyclization melt is then hydrolyzed by adding dropwise 300 parts of water as described in Example 3. The suspension obtained is stirred for a further 3 hours at about 60° C. and then poured into a mixture of 800 parts of water and 15 parts of kieselguhr, 15 parts of charcoal are added and the whole is filtered. The filtrate is added to 300 parts of 25% aqueous ammonia solution, the colorless precipitate formed is filtered off with suction, washed with a small amount of water and dried.

141.6 Parts (85.7% of the theory) of 2,6-diaminobenzthiazole having a melting point of 207° C. and a purity of over 95% are obtained.

EXAMPLE 5

When the reaction is carried out as described in Example 4, but instead of 4-aminophenylthiourea an equimolar amount of 5-amino-1-naphthylthiourea is used, 2,6-diaminonaphtho[1,2-d]thiazole is obtained in an equally good yield and quality.

EXAMPLE 6

186.5 Parts of 3-chloro-phenylthiourea are added while stirring over a period of 90 minutes to 334.6 parts of thionyl chloride of about 65° C. and the mixture is refluxed (65° to 70° C.) for 5 hours while stirring. The cyclization melt obtained is hydrolyzed as described in Example 1 with 3,200 parts of water and further treated as described in said example. 170.3 Parts (92.3% of the theory) of a mixture of 5- to 7-chloro-2-aminobenzothiazoles free from detectable impurities are obtained.

EXAMPLE 7

When the reaction is carried out as described in Example 6 but, instead of 3-chlorophenylthiourea, the same amount of 4-chlorophenylurea is used, 173.4 parts (corresponding to 94.0% of the theory) of 6-chloro-2-aminobenzthiazole melting at 205° C. and having a degree of purity of 98.9%, determined by potentiometric titration with perchloric acid, are obtained.

EXAMPLES 8 to 22

Compounds according to formula (3) indicated in the following Examples of the Table, are obtained by the process of the invention, for example, by a process variant as described in any one of the preceding Examples, in the yield and degree of purity indicated in the Table using as starting compounds the corresponding phenylthioureas according to formula (4)

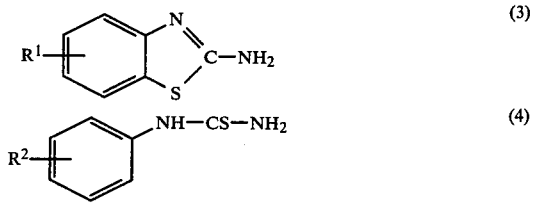

gases (sulfur dioxide and hydrogen chloride) are tranformed into aqueous hydrochloric acid and sodium sulfite solution in a two-stage absorption apparatus (using water, respectively an aqueous sodium hydroxide solution).

The cyclization melt is added while stirring to a mixture of 2,700 parts of water and 40 parts of kieselguhr, stirring of the mixture is continued for 30 minutes at 60° C., the mixture is clarified with 10 parts of charcoal, filtered and the filtrate is added to 350 parts of 25% aqueous ammonia solution. The 3-ethyl-2-iminobenzthiazoline precipitates in the form of colorless crystals which are filtered off, washed with water and dried. 341.7 Parts (96.0% of the theory) of 3-ethyl-2-iminobenzthiazole melting at 85° C. and having a degree of purity of over 99.5% according to potentiometric titration with perchloric acid are obtained.

EXAMPLE 24

When the reaction is carried out as described in Example 23 with the exception that instead of N-ethyl-N-phenylthiourea an equimolar amount of N-methyl-N-phenylthiourea is used, 3-methyl-2-iminobenzthiazoline melting at 122° C. is obtained in a yield of 95.6% and with an equally good purity.

EXAMPLE 25

180 Parts of N-(2-methylphenyl)-N-methylthiourea are uniformly added over a period of 3 hours at 20° to 30° C. to 298.7 parts of thionyl chloride. The reaction mixture is then heated to 45° to 50° C. within 2 hours and stirring at said temperature is continued for 3 hours. 250 Parts of water are added dropwise to the reaction product over a period of 2 hours. The escaping reaction gases are absorbed as described in Example 23. The suspension formed is then added while stirring to a

| Ex. | $R_1$ | $R_2$ | yield (% of theory) | degree of purity | m.p. °C. |
|---|---|---|---|---|---|
| 8 | H | H | 93.2 | 99.1% | 130 |
| 9 | 6-(i-$C_4H_9$) | 4-(i-$C_4H_9$) | 88.7 | 98.5% | 140 |
| 10 | 4-n-$OC_4H_9$ | 2-n-$OC_4H_9$ | 94.0 | 99.4% | 144 |
| 11 | 6-i-$C_5H_{11}$ | 4-i-$C_5H_{11}$ | 93.2 | 99.5% | 122 |
| 12 | 5- and 7-$CH_3$ | 3-$CH_3$ | 87.0 | — | — |
| 13 | 6-i-$OC_3H_7$ | 4-i-$OC_3H_7$ | 85.5 | 94.9% | 135 |
| 14 | 6-$CH_3$ | 4-$CH_3$ | 96.4 | 99.2% | 140 |
| 15 | 6-NH—CO—$CH_3$ | 4-NH—CO—$CH_3$ | 90.0 | 97.5% | 239 |
| 16 | 6-S-$C_2H_5$ | 4-S-$C_2H_5$ | 92.7 | 99.0% | 171 |
| 17 | 6-CO—O—$C_2H_5$ | 4-CO—O—$C_2H_5$ | 81.2 | 95.2% | 241 |
| 18 | 6-OC—$CH_3$ | 4-OC—$CH_3$ | 93.8 | 98.0% | 178 |
| 19 | 6-CO—O—$CH_3$ | 4-CO—O—$CH_3$ | 79.4 | 98.9% | 200 |
| 20 | 4,5-benzo | 2,3-benzo | 92.0 | 98.2% | 186 |
| 21 | 6-Br | 4-Br | 98.1 | 99.0% | 212 |
| 22 | 6-N($CH_3$)$_2$ | 4-N($CH_3$)$_2$ | 81.7 | 90.1% | 176 |

EXAMPLE 23

360 Parts of N-ethyl-N-phenylthiorea are uniformly added at 50° to 60° C. over a period of 2 hours to 666.4 parts of thionyl chloride and the suspension obtained is stirred for 4 hours at 50° to 60° C. The escaping reaction mixture of 1,000 parts of water and 20 parts of kieselguhr, 5 parts of charcoal are added and the whole is stirred for 30 minutes at about 60° C. The mixture is then filtered and the filtrate is adjusted to pH 8.5 by adding dropwise an aqueous about 30% sodium hydroxide solution. The precipitate formed is filtered off with suction at 20° C., washed with water and dried.

162.5 Parts (91.3% of the theory) of 3,4-dimethyl-2-iminobenzthiazoline melting at 83.5° C. and having a purity of over 98.5% are obtained.

3,4-Dimethyl-2-iminobenzthiazoline is also obtained from the reaction melt in an equally good yield and quality when the melt is forced into 1,250 parts of water containing 20 parts of kieselguhr and otherwise proceeding as indicated above.

EXAMPLE 26

210 Parts of N-(4-methoxyphenyl)-N-ethyl-thiourea are added over a period of 4 hours while stirring to 394.4 parts of thionyl chloride of about 50° C., stirring of the mixture is continued for 4 hours at about 50° C. and the cyclization melt is hydrolyzed by adding dropwise 300 parts of water as indicated in Example 25. The suspension obtained is stirred for a further 3 hours at about 60° C. and then added to a mixture of 800 parts of water and 15 parts of kieselguhr. Next, 15 parts of charcoal are added for clarification and the mixture is filtered. The filtrate is added to 300 parts of 25% aqueous ammonia solution, the colorless precipitate formed is filtered off with suction, washed with a small amount of water and dried.

182.0 Parts (87.5% of the theory) of 6-methoxy-3-ethyl-2-iminobenzthiazoline melting at 60° C. and having a purity of over 95% are obtained.

EXAMPLE 27

When the reaction is carried out as described in Example 26 using, instead of N-(4-methoxyphenyl)-N-ethylthiourea, an equimolar amount of N-(4-chlorophenyl)-N-methyl-thiourea, the corresponding 6-chloro-3-methyl-2-iminobenzthiazoline having a melting point of 79° C. is obtained in an equally good yield and quality.

EXAMPLE 28

125.5 Parts of N-phenyl-N-(β-diethylaminoethyl)-thiourea are added within 90 minutes while stirring to 334.6 parts of thionyl chloride of about 65° C. and stirring of the reaction mixture is continued for 5 hours under reflux (65° to 70° C.). Next, the cyclization melt obtained is hydrolyzed with 3,200 parts of water under the conditions of Example 23. When the clarified aqueous solution is added to ammonia, the final product separates in the form of an oil. By distillation under reduced pressure of 0.133 millibar at a boiling temperature of 190° C., 102.5 parts (82.3% of the theory) of 3-(β-diethyl-aminoethyl)-2-iminobenzthiazoline are obtained. In the gas chromatogram no detectable impurities can be found.

EXAMPLE 29

When proceding as described in Example 28 with the exception that N-phenyl-N-(β-diethylaminoethyl)-thiourea is replaced by an equivalent amount of N-(2-ethoxyphenyl)-N-methyl-thiourea, 98.7 parts (94.0% of the theory) of 4-ethoxy-3-methyl-2-iminobenzthiazoline having a boiling point of 180° C. at 0.066 millibar and a degree of purity of 98.9%, determined by potentiometric titration with perchloric acid, are obtained.

EXAMPLES 30 to 52

Compounds according to formula (3a) indicated in the following Examples of the Table, are obtained by the process of the invention, for example, analogously to a method as described in any one of the preceding Examples, in the yield and purity indicated in the Table using as starting compounds the corresponding phenyl-thioureas according to formula (4a)

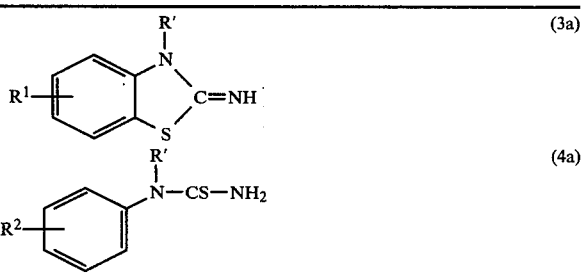

| Ex. | R' | R¹ | R² | Yield (% of theory) | purity | m.p. or b.p. (mbar) |
|---|---|---|---|---|---|---|
| 30 | n-C$_3$H$_7$ | H | H | 93.1 | 98.9% | 166° C. |
| 31 | n-C$_4$H$_9$ | H | H | 89.7 | 98.2% | 157° C. (5.33) |
| 32 | i-C$_5$H$_{11}$ | H | H | 81.0 | 97.9% | 165° C. (4.0) |
| 33 | —CH$_2$—CH$_2$OH | H | H | 95.6 | 99.0% | 120° C. |
| 34 | —CH$_2$—C$_6$H$_5$ | H | H | 94.1 | 98.0% | 79° C. |
| 35 | phenyl | H | H | 89.5 | 95.3% | 208° C. |
| 36 | cyclohexyl | H | H | 82.9 | 98.1% | 104° C. |
| 37 | —CH$_3$ | 6-Br | 4-Br | 93.0 | 95.6% | 106° C. |
| 38 | —CH$_3$ | 6-CH$_3$ | 4-CH$_3$ | 92.5 | 98.3% | 50° C. |
| 39 | —CH$_3$ | 4-CH$_3$ + 6-CH$_3$ | 2-CH$_3$ + 4-CH$_3$ | 88.8 | 97.0% | 104° C. |
| 40 | —CH$_3$ | 6-phenyl | 4-phenyl | 97.4 | 92.8% | 166° C. |
| 41 | —CH$_3$ | 6-OC$_2$H$_5$ | 4-OC$_2$H$_5$ | 81.0 | 99.4% | 200° C. (0.006) |
| 42 | —C$_2$H$_5$ | 6-CH$_3$ | 4-CH$_3$ | 91.0 | 96.6% | 104° C. |
| 43 | —C$_2$H$_5$ | 4-OCH$_3$ | 2-OCH$_3$ | 87.5 | 94.8% | 40° C. |
| 44 | —C$_2$H$_5$ | 5-OCH$_3$ | 3-OCH$_3$ | 69.0 | 97.8% | 56° C. |
| 45 | —(CH$_2$)$_2$—N(CH$_3$)$_2$ | 6-OC$_2$H$_5$ | 4-OC$_2$H$_5$ | 71.4 | 98.9% | 198° C. (0.5) |
| 46 | —(CH$_2$)$_2$—N(CH$_3$)$_2$ | 6-Cl | 4-Cl | 90.0 | 97.8% | 146° C. (0.009) |
| 47 | —(CH$_2$)$_2$—N(CH$_3$)$_2$ | 6-COOC$_2$H$_5$ | 4-COOC$_2$H$_5$ | 93.9 | 98.7% | 165° C. (0.003) |

-continued

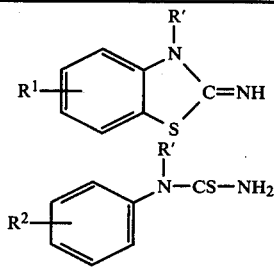

(3a)

(4a)

| Ex. | R' | R¹ | R² | Yield (% of theory) | purity | m.p. or b.p. (mbar) |
|---|---|---|---|---|---|---|
| 48 | —(CH₂)₃—N(CH₃)₂ | 5-Cl | 3-Cl | 58.9 | 99.2% | 167° C. (1.06) |
| 49 | —(CH₂)₃—N(CH₃)₂ | 6-Cl | 4-Cl | 88.2 | 98.2% | 150° C. (0.066) |
| 50 | —(CH₂)₃—N(CH₃)₂ | 6-COOC₂H₅ | 4-COOC₂H₅ | 90.6 | 96.2% | 168° C. (0.0026) |
| 51 | 2-CH₃-C₆H₄- | 4-CH₃ | 2-CH₃ | 93.9 | 91.9% | 62° C. |
| 52 | 3-CH₃-C₆H₄- | 6-CH₃ | 4-CH₃ | 88.7 | 95.0% | 73° C. |

EXAMPLE 53

328 Parts of N'-methyl-N-phenylthiourea are uniformly added, at 50° to 60° C. over a period of 2 hours, to 666.4 parts of thionyl chloride and the suspension obtained is stirred for 4 hours at 50° to 60° C. The escaping reaction gases (sulfur dioxide and hydrogen chloride) are transformed in a two-stage absorption apparatus with the use of water, respectively of an aqueous sodium hydroxide solution) into aqueous hydrochloric acid and sodium bisulfite solution.

Next, the cyclization melt is poured while stirring into a mixture of 2,700 parts of water and 40 parts of kieselguhr, stirring is continued for 30 minutes at 60° C., the mixture is clarified with 10 parts of charcoal and filtered. The filtrate is added to 350 parts of 25% aqueous ammonia solution, whereby the 2-methylamino-benzthiazole precipitates in the form of colorless crystals, which are filtered off, washed with water and dried. 310.9 Parts (94.8% of the theory) of 2-methylamino-benzthiazole melting at 137° C. and having a purity of over 99.5% according to potentiometric titration with perchloric acid are obtained.

EXAMPLE 54

When operating as described in Example 53, using instead of N'-methyl-N-phenylthiourea an equimolar amount of N'-ethyl-N-phenylthiourea, 2-ethylamino-benzthiazole melting at 93° C. is obtained in a yield of 94.4% of the theory and with an equally good purity.

EXAMPLE 55

254 Parts of N,N'-bis-(p-tolyl)-thiourea are uniformly added, at 20° to 30° C. over a period of 3 hours, to 298.7 parts of thionyl chloride, the reaction mixture is heated to 45° to 50° C. within 2 hours and stirring is continued for 3 hours at that temperature. 250 Parts of water are then added dropwise to the reaction product over a period of 2 hours, while the temperature is maintained in the range of from 50° to 60° C. The escaping reaction gases are absorbed as described in Example 53. The suspension formed is then added while stirring to a mixture of 1,000 parts of water and 20 parts of kieselguhr, 5 parts of charcoal are added and the whole is stirred for 30 minutes at about 60° C. The reaction mixture is then filtered and the filtrate is adjusted to pH 8.5 by the dropwise addition of an aqueous sodium hydroxide solution of about 30% strength. The precipitate formed is filtered off with suction at 20° C., washed with water and dried.

233.4 Parts (91.9% of the theory) of 6-methyl-2-(p-tolyl-amino)-benzthiazole melting at 169° C. and having a purity of over 99.5% are obtained.

6-Methyl-2-(p-tolylamino)-benzthiazole is obtained from the above reaction melt in an equally good yield and quality when the melt is forced into 1,250 parts of water containing 20 parts of kieselguhr and the further treatment is continued under otherwise unchanged conditions.

EXAMPLE 56

178 Parts of N',N'-dimethyl-N-phenylthiourea are added while stirring over a period of 4 hours to 394.4 parts of thionyl chloride of approximately 50° C., stirring is continued for 4 hours at about 50° C. and the cyclization melt is hydrolyzed by adding dropwise 300 parts of water as described in Example 3. The suspension obtained is stirred for a further 3 hours at about 60° C., poured into a mixture of 800 parts of water and 15 parts of kieselguhr, admixed with 15 parts of charcoal and filtered. The filtrate is added to 300 parts of 25% aqueous ammonia solution, the colorless precipitate formed is filtered off with suction, washed with a small amount of water and dried.

169.1 Parts (95.0% of the theory) of 2-(dimethylamino)-benzthialzole melting at 86° C. and having a purity of over 95% are obtained.

EXAMPLE 57

When operating as described in Example 56, using instead of N',N'-dimethyl-N-phenylthiourea, an equimolar amount of N',N'-dimethyl-N-(1-naphthyl)-thiourea, the corresponding 2-(dimethylamino)-naphtho[1,2-d]thiazole melting at 136°-138° C. is obtained in an equally good yield and quality.

EXAMPLE 58

240.0 Parts of N'-benzyl-N-phenylthiourea are added, while stirring, over a period of 90 minutes to 334.6 parts of thionyl chloride of approximately 65° C. The reaction mixture is then refluxed (65° to 70° C.) for 5 hours while stirring. The cyclization melt obtained is hydrolyzed with 3,200 parts of water analogously to Example 53 and further treated as described in said Example. 221.5 Parts (92.3% of the theory) of 2-benzylaminobenzthiazole melting at 159° C. are obtained.

EXAMPLE 59

When proceding as described in Example 58, using instead of N'-benzyl-N-phenylthiourea an equivalent amount (232.0 parts) of N'-cyclohexyl-N-phenylthiourea, 218.1 part (94.0% of the theory) of 2-cyclohexylaminobenzthiazole melting at 95° C. and having a purity of 98.9%, as ascertained by potentiometric titration with perchloric acid, are obtained.

EXAMPLES 60 to 88

Compounds according to formula (3b) indicated in the following Examples of the Table, are obtained by the process of the invention, for example, analgously to a method as described in any one of the preceding Examples, in the yield and purity indicated in the Table, using as starting compounds the corresponding arylthioureas according to formula:

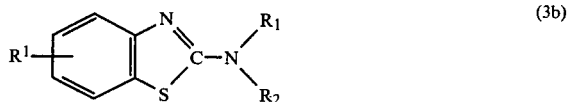
(3b)

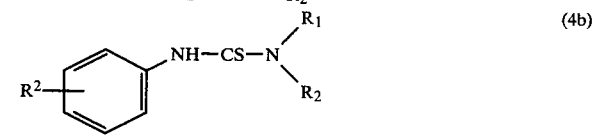
(4b)

| Example | $R_1$ | $R_2$ | $R_1$ | $R_2$ | Yield (% of theory) | purity | m.p. |
|---|---|---|---|---|---|---|---|
| 60 | H | H | $-C_2H_5$ | H | 93.2 | 99.1% | 93° C. |
| 61 | H | H | $n-C_3H_7$ | H | 88.7 | 98.5% | 68° C. |
| 62 | H | H | $n-C_4H_9$ | H | 94.0 | 99.4% | 86° C. |
| 63 | H | H | $i-C_4H_9$ | H | 93.2 | 99.5% | 101° C. |
| 64 | H | H | $n-C_6H_{13}$ | H | 87.0 | 96.7% | 64° C. |
| 65 | H | H | Phenyl | H | 95.8 | 94.9% | 161° C. |
| 66 | H | H | —⟨C₆H₄⟩—Cl | H | 96.4 | 99.2% | 197° C. |
| 67 | 4-F | 6-F | —⟨C₆H₄⟩—F | H | 90.0 | 97.5% | 225° C. |
| 68 | 4-Cl | 6-Cl | —⟨C₆H₄⟩—Cl | H | 92.7 | 99.0% | 223° C. |
| 69 | 4-Br | 6-Br | $-CH_3$ | H | 81.2 | 95.2% | 225° C. |
| 70 | 4-Br | 6-Br | $-C_2H_5$ | H | 93.8 | 98.0% | 157° C. |
| 71 | 4-Br | 6-Br | $n-C_4H_9$ | H | 79.4 | 98.9% | 118° C. |
| 72 | 4-Br | 6-Br | —⟨C₆H₄⟩—Br | H | 92.0 | 98.2% | 257° C. |
| 73 | 4-Cl | 6-Cl | $-CH_3$ | $-CH_3$ | 98.1 | 99.0% | 99° C. |
| 74 | 4-Br | 6-Br | $-CH_3$ | $-CH_3$ | 81.7 | 90.1% | 166° C. |
| 75 | 4-CH₃ | 6-CH₃ | $-CH_3$ | $-CH_3$ | 94.0 | 92.8% | 86° C. |
| 76 | 2-CH₃ | 4-CH₃ | $n-C_3H_7$ | H | 85.8 | 93.0% | 62° C. |
| 77 | 2,3-benzo | 4,5-benzo | $-C_2H_5$ | H | 92.7 | 90.8% | 106° C. |
| 78 | 2,3-benzo | 4,5-benzo | $n-C_4H_9$ | H | 98.7 | 92.1% | 67° C. |
| 79 | H | H | $-(CH_2)_3-OCH_3$ | H | 79.9 | 98.5% | 88° C. |
| 80 | H | H | $-(CH_2)_2-Cl$ | H | 87.0 | 92.3% | 59° C. |
| 81 | 4-OCH₃ | 6-OCH₃ | $-CH_3$ | H | 91.9 | 96.5% | 180° C. |
| 82 | 4-OCH₃ | 6-OCH₃ | $-CH_3$ | $-CH_3$ | 90.2 | 97.1% | 143° C. |
| 83 | 4-OC₂H₅ | 6-OC₂H₅ | $-CH$ | H | 87.8 | 96.5% | 145° C. |
| 84 | 4-OC₂H₅ | 6-OC₂H₅ | $-CH_3$ | $-CH_3$ | 92.1 | 96.3% | 118° C. |
| 85 | 4-OC₂H₅ | 6-OC₂H₅ | $n-C_4H_9$ | H | 88.0 | 95.7% | 100° C. |
| 86 | 4-OH | 6-OH | $-CH_3$ | $-CH_3$ | 89.7 | 90.3% | 255° C. |
| 87 | 4-OH | 6-OH | $-C_2H_5$ | $-C_2H_5$ | 90.2 | 92.0% | 145° C. |
| 88 | 4-OC₄H₉(n) | 6-OC₄H₉(n) | $-CH_3$ | H | 93.5 | 96.8% | 116° C. |

EXAMPLE 89

182 Parts of 4-methoxyphenyl-thiourea are suspended in 900 parts of toluene; 310 parts of thionyl chloride are added over a period of 1 hour at 20° to 30° C. The temperature of the mixture is then uniformly raised to 110° C. within 2 hours while stirring, stirring is continued for 2 hours under reflux, 20 parts of kieselguhr are added and the toluene is distilled off by blowing in steam. The solution of 6-methoxy-2-aminobenzthiazole hydrochloride obtained is clarified by adding 5 parts of charcoal, filtered and the clear filtrate is added to 175 parts of 25% aqueous ammonia solution.

The 6-methoxy-2-aminobenzthiazole precipitates in the form of colorless crystals which are filtered off, washed with water and dried. 173 Parts (96.1% of the theory) of 6-methoxy-2-aminobenzthiazole melting at 162° C. and having a purity of over 99.5%, determined by potentiometric titration, are obtained.

EXAMPLE 90

When, instead of the toluene as used in Example 89, corresponding amounts of chlorobenzene, ethylene chloride or xylene are used, the benzthiazole compound is obtained in an equally good yield and quality.

EXAMPLE 91

When using, instead of 4-methoxyphenyl-thiourea of Examples 89 and 90, equivalent amounts of N-phenyl-N'-methyl-thiourea or N-phenyl-N-methyl-thiourea, the other conditions remaining the same, 2-methylamino-benzthiazole (m.p. 137° C.) or 3-methyl-2-imino-benzthiazoline (m.p. 122°) is obtained in an equally good yield and in a high purity.

What is claimed is:

1. In a process for the manufacture of a 2-amino-benzthiazole compound of the formula (2a) or of a 2-imino-benzthiazoline compound of the formula (2b)

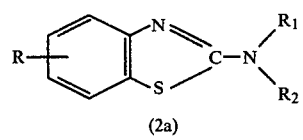

(2a)

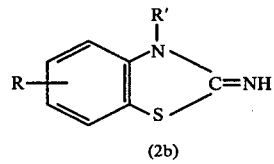

(2b)

in which R is hydrogen, fluorine, chlorine, bromine, lower alkyl, lower alkoxy, hydroxy or amino, $R_1$ and $R_2$ are identical or different from each other and $R_1$ is hydrogen and $R_2$ is hydrogen, lower alkyl, cyclohexyl, phenyl unsubstituted or substituted by one or two substituents selected from the group of methyl, ethyl, methoxy, ethoxy and chlorine, R' is hydrogen or alkyl of from 1 to 4 carbon atoms, unsubstituted or substituted by phenyl, hydroxy or amino of the formula —$NR_3R_4$ in which $R_3$ and $R_4$ are identical or different from each other and $R_3$ is alkyl of from 1 to 4 carbon atoms, benzyl or phenyl and $R_4$ is alkyl of from 1 to 4 carbon atoms, or R' is cyclohexyl or phenyl, comprising cyclization of a phenyl-thiourea compound of the formula (1a) or of the formula (1b)

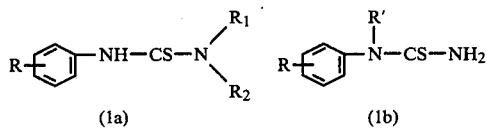

in which R, R', $R_1$ and $R_2$ are defined as above, the improvement consisting of carrying out the cyclization reaction by reacting the phenylthiourea compound with 2.1 to 5 mols of thionyl chloride at a temperature of from 40° to 80° C.

2. A process as claimed in claim 1, wherein a compound of the formula

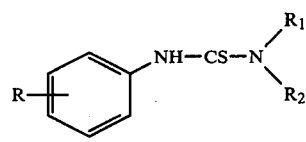

in which $R_1$ is hydrogen and $R_2$ is lower alkyl, cyclohexyl or phenyl and R is hydrogen, fluorine, chlorine, bromine, lower alkyl, lower alkoxy, hydroxy or amino, is cyclized to a compound of the formula

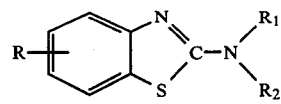

in which R, $R_1$ and $R_2$ have the aforesaid meaning.

3. A process according to claim 1, wherein the cyclization reaction is carried out in the absence of an organic solvent.

4. A process according to claim 1 wherein the reaction product is contacted with water.

* * * * *